(12) United States Patent
Nobles (10) Patent No.: US 12,398,351 B2
(45) Date of Patent: Aug. 26, 2025

(54) METHODS AND DEVICES FOR PAPILLARY SUTURING

(71) Applicant: HeartStitch, Inc., Fountain Valley, CA (US)

(72) Inventor: Anthony A. Nobles, St. Thomas, VI (US)

(73) Assignee: HeartStitch, Inc., Fountain Valley, CA (US)

( * ) Notice: Subject to any disclaimer, the term of this patent is extended or adjusted under 35 U.S.C. 154(b) by 91 days.

(21) Appl. No.: 18/114,875

(22) Filed: Feb. 27, 2023

(65) Prior Publication Data
US 2023/0279319 A1  Sep. 7, 2023

Related U.S. Application Data

(63) Continuation of application No. 16/646,126, filed as application No. PCT/US2018/050210 on Sep. 10, 2018, now Pat. No. 11,591,554.
(Continued)

(51) Int. Cl.
*A61B 17/04* (2006.01)
*A61B 17/00* (2006.01)
(Continued)

(52) U.S. Cl.
CPC .......... *C12H 1/003* (2013.01); *A61B 17/0469* (2013.01); *A61B 17/062* (2013.01);
(Continued)

(58) Field of Classification Search
CPC .............. A61B 17/0469; A61B 17/062; A61B 2017/047; A61B 2017/06042; A61F 2/2457
See application file for complete search history.

(56) References Cited

U.S. PATENT DOCUMENTS 5,860,992 A   1/1999  Daniel
5,868,762 A   2/1999  Cragg
(Continued)

FOREIGN PATENT DOCUMENTS

EP   2528511 A1   12/2012
EP   2413809 B1   10/2014
(Continued)

OTHER PUBLICATIONS

Joshi, Devang J., et al., *A Novel Minimal Access Cardiac Surgery Automated Suturing Device with a Needle Sheath to Minimize the Risk of Needle-Stick Injuries*, Annual Meeting Posters, IS ISMICS annual scientific meeting, Jun. 3-6, 2015; as available on Jul. 25, 2015 by the Wayback Machine Internet Archive, accessed on Mar. 16, 2022. https://web.archive.org/web/20150625011714/https://meetings.ismics.org/abstracts/2015/P21.cgi.
(Continued)

*Primary Examiner* — Darwin P Erezo
*Assistant Examiner* — Raihan R Khandker
(74) *Attorney, Agent, or Firm* — Knobbe, Martens, Olson & Bear LLP (57) ABSTRACT

A minimally invasive device and method for suturing papillary muscles includes drawing a suture through a first papillary muscle using a needle, drawing the suture through a second papillary muscle, and tightening the suture to move at least one of the first papillary muscle and the second papillary muscle towards the other of the first papillary muscle and the second papillary muscle.

9 Claims, 4 Drawing Sheets

Related U.S. Application Data (60) Provisional application No. 62/556,979, filed on Sep. 11, 2017.

(51) Int. Cl.

| | |
|---|---|
| *A61B 17/06* | (2006.01) |
| *A61B 17/062* | (2006.01) |
| *C12H 1/00* | (2006.01) |
| *C12N 9/02* | (2006.01) |
| *C12N 9/06* | (2006.01) |
| *C12N 9/78* | (2006.01) |

(52) U.S. Cl.
CPC ......... *C12N 9/0028* (2013.01); *C12N 9/0083* (2013.01); *C12N 9/78* (2013.01); *C12Y 105/01041* (2013.01); *C12Y 114/9904* (2013.01); *C12Y 305/99001* (2013.01); *A61B 2017/00243* (2013.01); *A61B 2017/047* (2013.01); *A61B 2017/06042* (2013.01)

(56) References Cited

U.S. PATENT DOCUMENTS

| | | |
|---|---|---|
| 5,908,428 A | 6/1999 | Scirica |
| 6,056,760 A | 5/2000 | Koike |
| 6,077,279 A | 6/2000 | Kontos |
| 6,840,246 B2 | 1/2005 | Downing |
| 6,896,686 B2 | 5/2005 | Weber |
| 6,991,635 B2 | 1/2006 | Takamoto |
| 7,063,710 B2 | 6/2006 | Takamoto |
| 7,232,448 B2 | 6/2007 | Battles |
| 7,544,199 B2 | 6/2009 | Bain |
| 7,635,386 B1 | 12/2009 | Gammie |
| 7,704,261 B2 | 4/2010 | Sakamoto |
| 7,935,128 B2 | 5/2011 | Rioux |
| 8,152,821 B2 | 4/2012 | Gambale |
| 8,313,498 B2 | 11/2012 | Pantages |
| 8,465,500 B2 | 6/2013 | Speziali |
| 9,078,752 B2 | 7/2015 | Hasenkam |
| 9,125,632 B2 | 9/2015 | Loulmet |
| 9,131,938 B2 | 9/2015 | Nobles |
| 9,326,764 B2 | 5/2016 | Nobles |
| 9,398,907 B2 | 7/2016 | Nobles |
| 9,572,667 B2 | 2/2017 | Solem |
| 9,706,988 B2 | 7/2017 | Nobles |
| 11,591,554 B2 | 2/2023 | Nobles |
| 2005/0059984 A1 | 3/2005 | Chanduszko |
| 2006/0259046 A1 | 11/2006 | de la Torre |
| 2007/0049952 A1 | 3/2007 | Weiss |
| 2007/0118151 A1 | 5/2007 | Davidson |
| 2008/0027468 A1 | 1/2008 | Fenton |
| 2008/0215069 A1* | 9/2008 | Gambale ................ A61B 17/08 |
| | | 606/144 |
| 2009/0099410 A1 | 4/2009 | De Marchena |
| 2010/0063586 A1 | 3/2010 | Hasenkam |
| 2010/0210899 A1* | 8/2010 | Schankereli .......... A61F 2/2487 |
| | | 128/898 |
| 2011/0011917 A1 | 1/2011 | Loulmet |
| 2011/0071626 A1 | 3/2011 | Wright |
| 2011/0288637 A1 | 11/2011 | De Marchena |
| 2013/0238001 A1* | 9/2013 | Nobles ............... A61B 17/0057 |
| | | 606/145 |
| 2014/0163585 A1 | 6/2014 | Nobles |
| 2014/0194906 A1 | 7/2014 | Topper |
| 2014/0276979 A1 | 9/2014 | Sauer |
| 2014/0371790 A1 | 12/2014 | Hatch |
| 2014/0379006 A1 | 12/2014 | Sutherland |
| 2015/0100071 A1 | 4/2015 | Phillips |
| 2015/0196294 A1 | 7/2015 | Murillo |
| 2015/0313620 A1 | 11/2015 | Suri |
| 2015/0359531 A1* | 12/2015 | Sauer ................. A61B 17/0469 |
| | | 606/148 |
| 2016/0143737 A1 | 5/2016 | Zentgraf |
| 2016/0324636 A1 | 11/2016 | Rourke |
| 2016/0345961 A1 | 12/2016 | Sauer |
| 2017/0049440 A1 | 2/2017 | Sauer |
| 2017/0245853 A1 | 8/2017 | Nobles |
| 2018/0311043 A1* | 11/2018 | Neustadter ............ A61M 25/09 |

FOREIGN PATENT DOCUMENTS

| | | |
|---|---|---|
| JP | 04088978 B2 | 5/2008 |
| WO | WO 2011/047201 A2 | 4/2011 |

OTHER PUBLICATIONS

Ozawa, Soji, et al., (2005). New endoscopic treatments for gastroesophageal reflux disease. Annals of thoracic and cardiovascular surgery: official journal of the Association of Thoracic and Cardiovascular Surgeons of Asia. 11. 146-53.

LSI Solutions, RD180 product device page as available on Mar. 20, 2016 by the Wayback Machine Internet Archive, accessed on Mar. 16, 2022. https://web.archive.org/web/20160320182253/https://www.lsisolutions.com/rd180deviceanatomy.

\* cited by examiner

METHODS AND DEVICES FOR PAPILLARY SUTURING

INCORPORATION BY REFERENCE TO ANY PRIORITY APPLICATIONS

The present application is a continuation of U.S. patent application Ser. No. 16/646,126, filed Mar. 10, 2020, which is a U.S. National Phase Application of International Patent Application No. PCT/US2018/050210, filed Sep. 10, 2018, which claims priority benefit of U.S. Provisional Application No. 62/556,979, filed Sep. 11, 2017, the entirety of which is hereby incorporated by reference.

BACKGROUND

Field

The present application relates to apparatuses and methods for suturing the papillary muscles of the heart, and more particularly, to minimally invasive apparatuses and methods for suturing the papillary muscles of the heart.

Description of the Related Art

Health practitioners frequently use sutures to close various openings such as cuts, punctures, and incisions in various places in the human body. Generally, sutures are convenient to use and function properly to hold openings in biological tissue closed thereby aiding in blood clotting, healing, and prevention of scarring.

SUMMARY

Methods, systems, and apparatuses are provided in certain embodiments of the present application to suture the papillary muscles of the heart.

In one embodiment, a minimally invasive method for suturing papillary muscles is provided. The method includes drawing a suture through a first papillary muscle using a needle, drawing the suture through a second papillary muscle, and tightening the suture to move at least one of the first papillary muscle and the second papillary muscle towards the other of the first papillary muscle and the second papillary muscle.

In another embodiment, a suturing device that can be inserted minimally invasively into the left ventricle of the heart for suturing of papillary muscles is provided. The suturing device includes a body, and a needle configured to extend out of the body and through a first side of a papillary muscle to engage a suture capture portion of a suture positioned on a second side of the papillary muscle.

In another embodiment, a suturing device that can be inserted minimally invasively into the left ventricle of the heart for suturing of papillary muscles is provided. The suturing device includes a first needle holder configured to receive a needle attached to a suture, a second needle holder configured to receive the needle attached to the suture, wherein the first needle holder and second needle holder are movable between a first configuration and a second configuration, and a driver configured to drive the needle from the first needle holder to the second needle holder in the first configuration and from the second needle holder to the first needle holder in the second configuration.

BRIEF DESCRIPTION OF THE DRAWINGS

The above-mentioned and other features disclosed herein are described below with reference to the drawings of specific embodiments. The illustrated embodiments are intended for illustration, but not limitation. The drawings contain the following figures.

DETAILED DESCRIPTION

Figure 1:
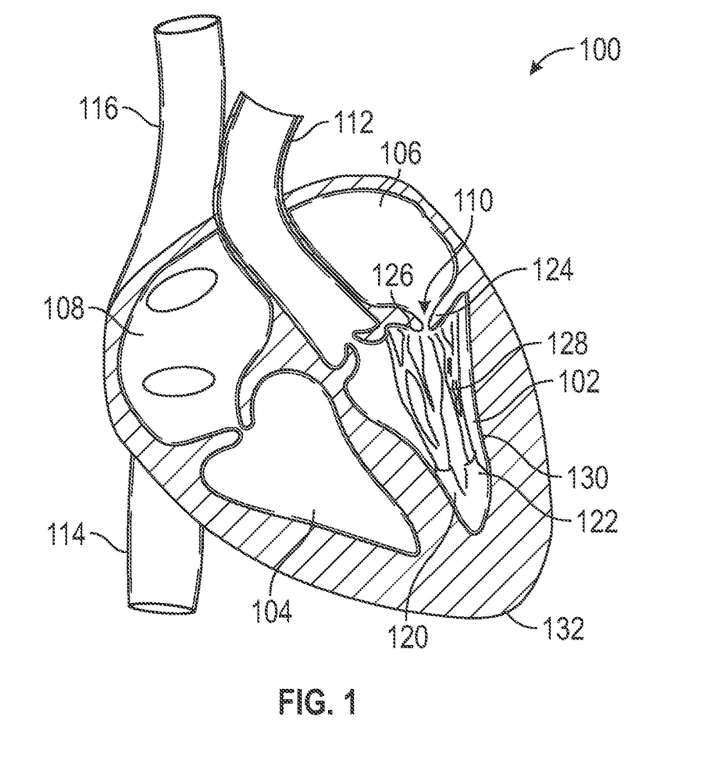
FIG. 1 depicts a schematic partial cross-sectional view of an exemplifying treatment area, comprising a human heart.

A human heart contains a number of papillary muscles that help the heart function properly. FIG. 1 depicts an image of a heart 100 having a left ventricle 102, a right ventricle 104, a left atrium 106, a right atrium 108, an aorta 112, an inferior vena cava 114, and a superior vena cava 116. A mitral valve 110 allows blood flow from the left atrium 106 to the left ventricle 102.

Figure 2:
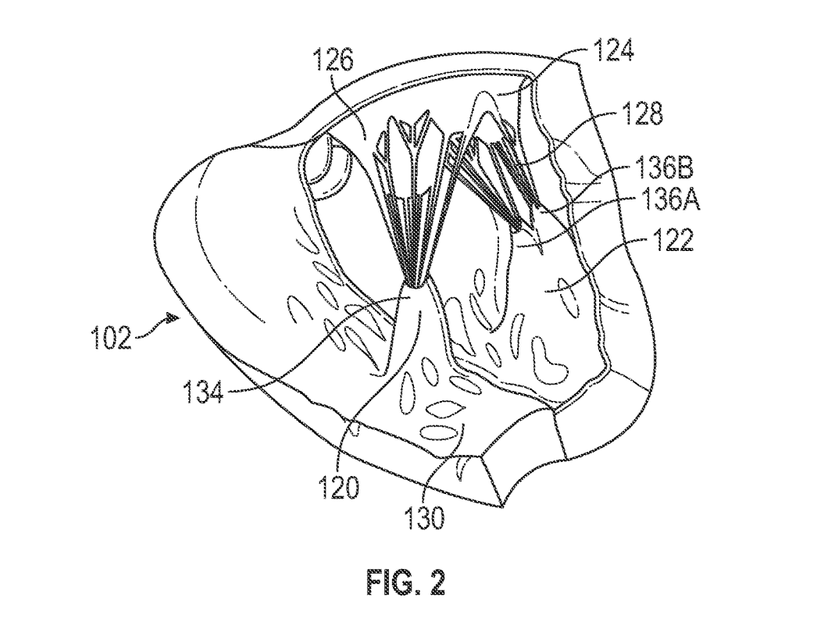
FIG. 2 depicts a perspective view of a section of a left ventricle of the human heart.

FIG. 2 depicts an interior section of the left ventricle 102. The left ventricle 102 includes two different papillary muscles, a posterior papillary muscle 122 and an anterior papillary muscle 120. The papillary muscles 122 and 120 project into the left ventricle 102 from the myocardium 130. As shown in FIG. 2, the posterior papillary muscle 122 has two papillary muscle projections 136A-B. The anterior papillary muscle 120 has a single papillary muscle projection 134. A posterior leaflet 124 of the mitral valve 110 and an anterior leaflet 126 of the mitral valve 110 extend into the left ventricle 100. The posterior papillary muscle 122 and anterior papillary muscle 120 are coupled to the posterior leaflet 124 and anterior leaflet 120, respectively, by chordae tendineae 128. The chordae tendineae 128 are cord-like structures extending between the papillary muscle projections 136A-B and the posterior leaflet 124 and between papillary muscle projection 134 and the anterior leaflet 126. When functioning normally, the papillary muscles 120 and 122 contract during ventricular systole to prevent prolapse of the mitral valve 110 via tension on the chordae tendineae 128. If the mitral valve 110 does not properly close during systole, mitral regurgitation, the abnormal backflow of blood from the left ventricle 100 into the left atrium 106, can occur.

In some embodiments, a minimally invasive method for suturing the papillary muscles 120 and 122 of the heart can include placing one or more sutures within the anterior papillary muscle 120 and the posterior papillary muscle 122 (or sections of the myocardium 130 adjacent the papillary muscles) using a device delivered through an apex 132 of the heart (at the bottom of the left ventricle 102), from the left atrium 106 and through the mitral valve 110, or another approach. After the sutures are placed, the one or more sutures can be tightened to cause one or both of the anterior papillary muscle 120 and the posterior papillary muscle 122 to move towards the other of the anterior papillary muscle 120 and the posterior papillary muscle 122 (e.g., bringing the anterior papillary muscle 120 and the posterior papillary muscle 122 closer together).

The suturing of the papillary muscles 120 and 122 can improve the function of a damaged or diseased mitral valve 110, for example, by increasing tension in the chordae tendineae 128 and/or repositioning dislocated papillary muscle projections 134 and/or 136A-B to their proper orientation to prevent or reduce mitral regurgitation. In some embodiments, suturing of the papillary muscles 120 and 122 can be performed in addition to an Alfieri stitch procedure or any other suitable procedure to improve mitral valve functioning. In an Alfieri stitch procedure, a suture is placed between a central segment of the anterior leaflet 126 and a central segment of a posterior leaflet 124 of the mitral valve 110 and tightened to bring the two segments together, resulting in two mitral valve orifices on opposing sides of adjoined segments.

In some embodiments, the method can include positioning a first capture portion of a suture, such as a loop tied into a section of or provided at the end of the suture, on a first side of a first one of the papillary muscles 120 and 122. The method can further include directing a needle through a second side of the first papillary muscle 120 or 122 so that the needle grasps the first capture portion of the suture and brings the suture through the papillary muscle 120 or 122.

In some embodiments, the method can include positioning a second capture portion of a suture, such as a loop tied into a section of or provided at the end of the suture, on a first side of the second one of the papillary muscles 120 and 122. The method can further include directing a needle through a second side of the second papillary muscle 120 or 122 so that the needle grasps the second capture portion of the suture and brings the suture through the second papillary muscle 120 or 122. In some embodiments, a single suture can include both the first capture portion and the second capture portion. In other embodiments, the first capture portion and the second capture portion can be disposed on different sutures.

In some embodiments, the needle can be directed through the papillary muscle using a suturing device having features similar to the NobleStitch EL device, that was designed to suture the septum primum or secundum of a patent foramen ovale of a heart, and adapted for us as a papillary suturing device. Such a suturing device can include an elongate body, one or more needles and one or more sections (or arms) configured to hold a capture portion of a suture. For example, in some embodiments, the papillary suturing device can include one or more arms that can extend from the papillary suturing device and can hold a suture capture portion. In some embodiments, the papillary suturing device can be activated to extend one of the needles through one of the papillary muscles 120 or 122 towards the suture capture portion held in one of the arms to grasp the suture capture portion. The needle can be retracted within the papillary suturing device to draw the suture through the papillary muscle 120 or 122.

Examples of such suturing devices are described in U.S. Pat. No. 9,131,938, which is hereby incorporated by reference in its entirety. Examples are also shown in FIGS. 3 and 4.

Figure 3:
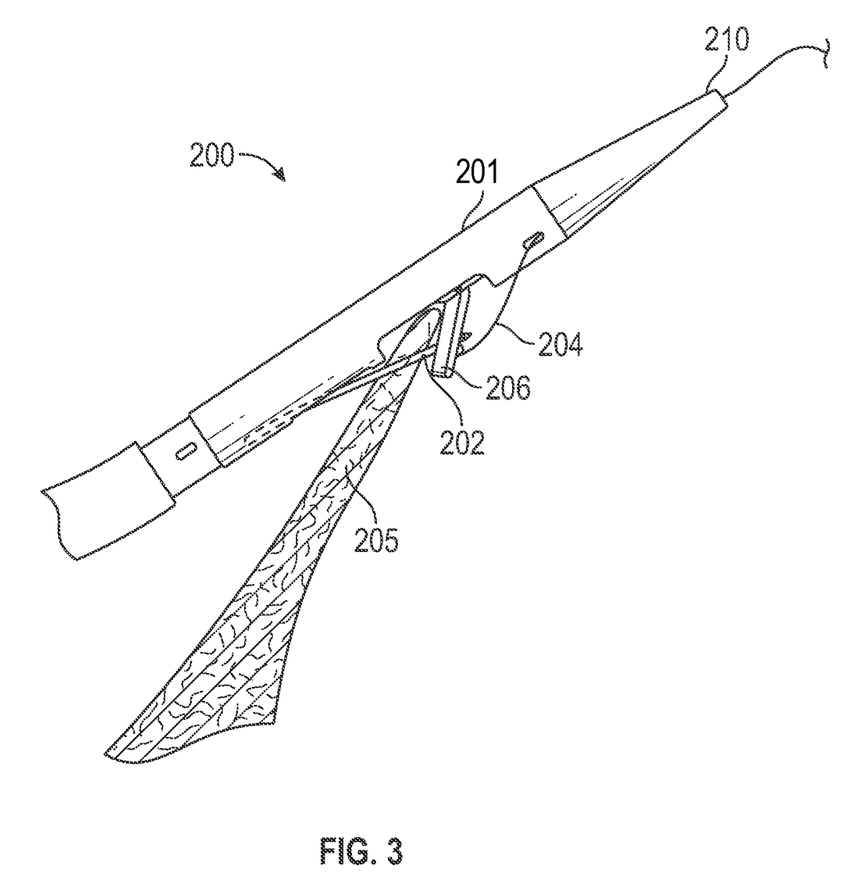
FIG. 3 depicts schematic representation of a distal portion of a suturing device 200 deployed in a tissue 205.
Figure 4:
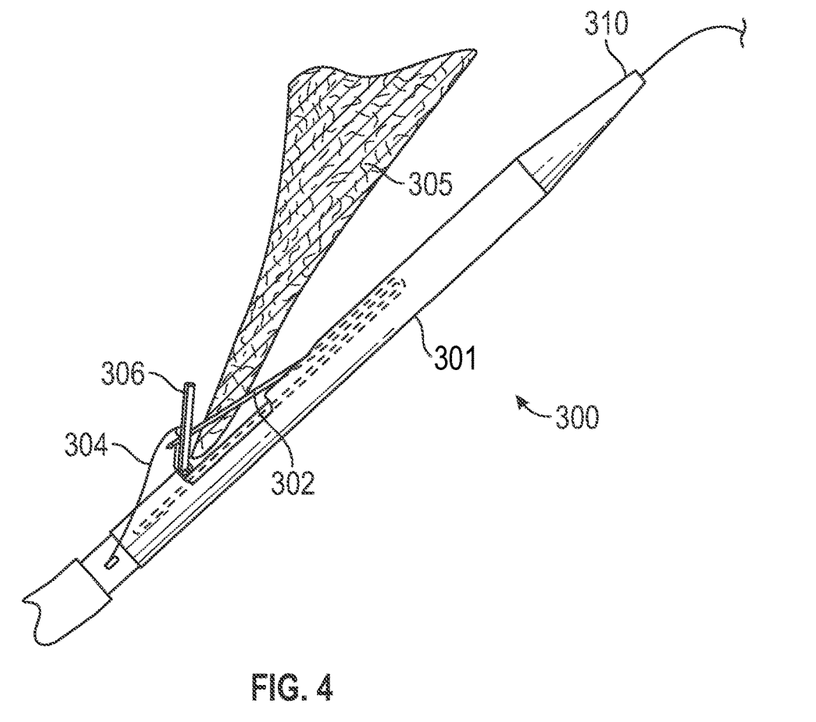
FIG. 4 depicts a schematic representation of a distal portion of a suturing device 300 deployed in a tissue 305.

FIG. 3 depicts a suturing device 200 according to one embodiment. The suturing device 200 can include a needle 202 and an arm 206 that can be used to apply a suture 204 to a tissue 205. In certain embodiments, the tissue 205 can be one of the papillary muscles 120 or 122.

In some embodiments, a suture capture portion of the suture 204 can be held by the arm 206. In some embodiments, the arm 206 can extend from a retracted position within a portion of an elongate body 201 of the suturing device 200 to an extended position. In some embodiments, when the arm 206 is in the extended position the suture capture portion can be positioned to receive the needle 202.

In some embodiments, the needle 202 can be advanced within a needle lumen of the suturing device 200 outwardly through an aperture in the body 201 of the suturing device 200. In some embodiments, the needle 202 can advance from the body 201 of the suturing device 200 and through the tissue 205 into engagement with the suture capture portion of the suture 204 held by the arm 206. As shown in FIG. 3, the needle 202 can advance out of the suturing device 200 towards a distal end 210 of the suturing device 200, and the arm 206 can angle back towards a proximal end (not shown) of the suturing device 200 when in the extended position. In some embodiments, in the extended position, the arm 206 can form an acute angle with a longitudinal axis of the body 201 of the suturing device 200.

In FIG. 3, the arm 206 is shown in the extended position, and the needle 202 is shown extending through the tissue 205 and engaged with the suture capture portion of the suture 204 held by the arm 206. After the needle 202 engages the suture capture portion, the needle 202 can be retracted through the tissue 205 to draw the suture 204 through the tissue 205.

In some embodiments, the suturing device 200 or modifications thereof can be used to draw the suture 204 through one of the papillary muscles 120 or 122 using a transapical approach (e.g., through a hole in the apex 132 of the heart 100). In some embodiments, a guidewire can be advanced into the left ventricle 102 using the transapical approach. After the guidewire is advanced into the left ventricle 102, the suturing device 200 can be advanced along the guidewire.

In some embodiments, the suturing device 200 can be positioned in the left ventricle 102 so that the arm 206 extends around a first side of the papillary muscle 120 or 122 when in the extended position. In some embodiments, the suturing device 200 can be positioned within the left ventricle 102 so that one of the papillary muscles 120 or 122 is positioned within a gap between the arm 206 and the body 201 of the suturing device 200 without interfering with the chordae tendineae 128. In some embodiments, the suturing device 200 can be advanced through the ventricle 102 around a side of the papillary muscle 120 or 122 prior to deployment of the arm 206 from the body 201 of the suturing device 200 and positioned so that the body 201 and arm 206 extend at an angle to a longitudinal axis extending between a proximal end of the papillary muscle 120 or 122 adjacent the heart wall and a distal end of the papillary muscle 120 or 122 to which the chordae tendineae 128 attach. In some embodiments, the suturing device 200 can be positioned in the left ventricle 102 so that the that the needle 202 can extend through a second side of the papillary muscle 120 or 122 to engage the suture capture portion of the suture 204 when the needle 202 is advanced out of the body 201 of the suturing device 200 and the arm 206 is in the extended position.

In some embodiments, the suturing device 200 can be used to suture both papillary muscles 120 and 122 so that the papillary muscles 120 and 122 can be drawn together. In some embodiments, the suturing device 200 can be used to suture a first papillary muscle 120 or 122 with the suture 204. In some embodiments, after suturing the first papillary muscle 120 or 122, the suturing device 200 can be reloaded with another suture or with another suture capture portion of the same suture 204 to suture the second papillary muscle 120 or 122. In some embodiments, a first suturing device 200 can be used to suture a first papillary muscle 120 or 122 and a second suturing device 200 can be used to suture a second papillary muscle 120 or 122.

In some embodiments, the suturing device 200 can include two arms 206. In some embodiments, a first arm 206 can be configured to suture a first papillary muscle 120 or 122, and a second arm 206 can be configured to suture a second papillary muscle 120 or 122. In some embodiments, the first arm 206 and second arm 206 can be configured to suture the first papillary muscle 120 or 122 and the second papillary muscle 120 or 122 sequentially. In some embodiments, each arm 206 can include a suture capture portion of the same suture 204 or a suture capture portion of a different suture.

FIG. 4 depicts a suturing device 300 according to one embodiment. The suturing device 300 can include a needle 302 and an arm 306 that can be used to apply a suture 304 to a tissue 305. In some embodiments, the tissue 305 can be one of the papillary muscles 120 or 122

In some embodiments, a suture capture portion of the suture 304 can be held by the arm 306. In some embodiments, the arm 306 can extend from a retracted position within a portion of an elongate body 301 of the suturing device 300 to an extended position. In some embodiments, when the arm 306 is in the extended position the suture capture portion can be positioned to receive the needle 302.

In some embodiments, the needle 302 can be advanced within a needle lumen of the suturing device 300 outwardly through an aperture in the body 301 of the suturing device 300. In some embodiments, the needle 302 can advance from the body 301 of the suturing device 300 and through the tissue 305 into engagement with the suture capture portion of the suture 304 held by the arm 306. As shown in FIG. 4, the needle 302 can advance out of the suturing device 300 towards a proximal end (not shown) of the suturing device 300, and the arm 306 can angle towards a distal end 310 of the suturing device 300 when in the extended position. In some embodiments, in the extended position, the arm 206 can form an acute angle with a longitudinal axis of the body 301 of the suturing device 200.

In FIG. 4, the arm 306 is shown in the extended position, and the needle 302 is shown extending through the tissue 305 and engaged with the suture capture portion of the suture 304 held by the arm 306. After the needle 302 engages the suture capture portion, the needle 302 can be retracted through the tissue 305 to draw the suture 304 through the tissue 305.

In some embodiments, the suturing device 300 can be used to draw the suture 304 through one of the papillary muscles 120 or 122 through a transseptal approach in which the suturing device 300 can extend from the left atrium 106 to the left ventricle 102. In some embodiments, a guidewire can be advanced into the left ventricle 102 using the transeptal approach. After the guidewire is advanced into the left ventricle 102, the suturing device 300 can be advanced along the guidewire.

In some embodiments, the suturing device 300 can be positioned so that the arm 306 extends around a first side of the papillary muscle 120 or 122 when in the extended position. In some embodiments, the suturing device 300 can be positioned within the left ventricle 102 so that one of the papillary muscles 120 or 122 is positioned within a gap between the arm 306 and the body 301 of the suturing device 300 without interfering with the chordae tendineae 128. In some embodiments, the suturing device 300 can be advanced through the ventricle 302 around a side of the papillary muscle 120 or 122 prior to deployment of the arm 306 from the body 301 of the suturing device 300 and positioned so that the body 301 and arm 306 extend at an angle to a longitudinal axis extending between a proximal end of the papillary muscle 120 or 122 adjacent the heart wall and a distal end of the papillary muscle 120 or 122 to which the chordae tendineae 128 attach. In some embodiments, the suturing device 300 can be positioned in the left ventricle 102 so that the needle 302 can extend through a second side of the papillary muscle 120 or 122 to engage the suture capture portion of the suture 304 when the needle 302 is advanced out of the body 301 of the suturing device 300 and the arm 306 is in the extended position.

In some embodiments, the suturing device 300 can be used to suture both papillary muscles 120 and 122 so that the papillary muscles 120 and 122 can be drawn together. In some embodiments, the suturing device 300 can be used to suture a first papillary muscle 120 or 122 with the suture 304. In some embodiments, after suturing the first papillary muscle 120 or 122, the suturing device 300 can be reloaded with another suture or with another suture capture portion of the same suture 304 to suture the second papillary muscle 120 or 122. In some embodiments, a first suturing device 300 can be used to suture a first papillary muscle 120 or 122 and a second suturing device 300 can be used to suture a second papillary muscle 120 or 122.

In some embodiments, the suturing device 300 can include two arms 306. In some embodiments, a first arm 306 can be configured to suture a first papillary muscle 120 or 122, and a second arm 306 can be configured to suture a second papillary muscle 120 or 122. In some embodiments, the first arm 306 and second arm 306 can be configured to suture the first papillary muscle 120 or 122 and the second papillary muscle 120 or 122 sequentially. In some embodiments, each arm 306 can include a suture capture portion of the same suture 304 or a suture capture portion of a different suture.

In some embodiments, the suturing devices 200 and 300 shown in FIGS. 3-4 can be used to suture the papillary muscles from different approaches (e.g., transapical v. transseptal). In certain embodiments, the suturing device 200 can be used to suture a first papillary muscle 120 or 122 using a transapical approach, and the suturing device 300 can be used to suture the second papillary muscle 120 or 122 using the transseptal approach.

In another embodiment, the papillary suturing device can include a bendable/steerable catheter configured to extend at least partially around one of the papillary muscle(s) 120 and/or 122. In particular, the catheter can be steered to wrap around (or lasso) a papillary muscle 120 or 122, and then pass a needle between portions of the catheter.

Figure 5:
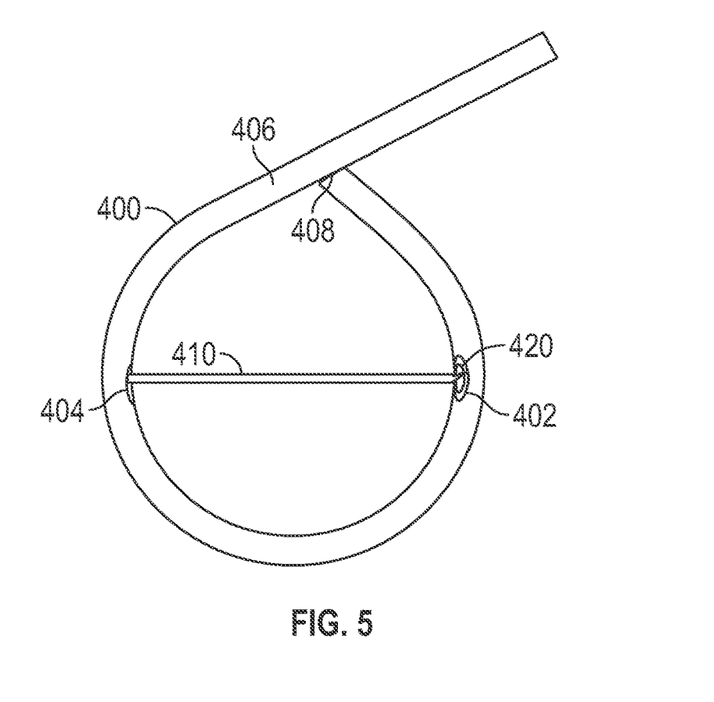
FIG. 5 depicts a top view of a suturing device 400.

FIG. 5 depicts a suturing device 400 according to one embodiment. In FIG. 5, the suturing device 400 is shown in a lassoed configuration in which the suturing device 400 is arranged around one of the papillary muscles 120 or 122. In some embodiments, the suturing device 400 can be configured to transition between a disengaged configuration and the lassoed configuration. In certain embodiments, the suturing device 400 can be straight or generally straight in the disengaged configuration. In certain embodiments, in the lassoed configuration, the suturing device 400 can be shaped, dimensioned, oriented, or otherwise configured to wrap around one of the papillary muscles 120 or 122 or at least partially wrap around the papillary muscle 120 or 122. In certain embodiments, in the lassoed configuration, a portion of the suturing device 400 can be bent or curved such that a distal end 408 of the suturing device 400 is directed towards a proximal portion 406 of the suturing 400. In certain embodiments, in the lassoed configuration, the distal end 408 of the suturing device 406 can contact the proximal portion 406. In some embodiments, the suturing device 400 can be a steerable catheter.

In some embodiments, the suturing device 400 can be steerable to navigate the body to the left ventricle 102. In some embodiments, the suturing device 400 can be steerable to advance to the left ventricle 102 via a transapical approach. In some embodiments, the suturing device 400 can be steerable to advance to the left ventricle 102 via a transseptal approach. In some embodiments, a guidewire can be advanced into the left ventricle 102. After the guidewire is advanced into the left ventricle 102, the suturing device 400 can be advanced along the guidewire into the left ventricle 102. In some embodiments, the suturing device 400 can be steerable to extend around, bend around or wrap around one of the papillary muscles 120 or 122. In some embodiments, the suturing device 400 can be advanced into the left ventricle 102 in the disengaged configuration. After the suturing device 400 is advanced into the left ventricle 102, the suturing device 400 can be manipulated to transition to the lassoed configuration so that the suturing device extends around, bends around, or wraps around the papillary muscle 120 or 122 in the lassoed configuration. For example, in some embodiments, after the suturing device 400 is advanced into the left ventricle 102, the distal end 408 of the suturing device 400 can advanced around the papillary muscle 120 or 122 and back towards the proximal portion 406 of the suturing device 400.

In some embodiments, the suturing device 400 can include a first opening 402 configured to hold a suture capture portion 420 adjacent to a first side of the papillary muscle 120 or 122 when the suturing device 400 is arranged at least partially around the papillary muscle 120 or 122. In some embodiments, the suture caption portion 420 can be a loop tied into a section of the suture. The suturing device 400 can also include a second opening 404 from which a needle 410 can extend through a second side of the papillary muscle 120 or 122 when the suturing device 400 is arranged at least partially around the papillary muscle 120 or 122. In some embodiments, the suturing device 400 can include a needle guide, such as a ramp, within the suturing device 400 positioned, shaped, or otherwise dimensioned to guide a path of the needle 410 out of the second opening 404. In some embodiments, the needle guide can be configured to guide the needle 410 along a straight path or relatively straight path out of the second opening 404. In some embodiments, the needle guide can be configured to guide the needle 410 along a curved or actuate path out of the second opening 404.

When the catheter 400 is arranged at least partially around the papillary muscle in the lassoed configuration, the second opening 404 can be oriented to align with the first opening 402 so that the needle 410 can be activated to extend through the papillary muscle 120 or 122 and grasp the suture capture portion 420. After the suture capture portion 420 is grasped by the needle 410, the needle 410 can be retracted to draw the suture through the papillary muscle 120 or 122.

In some embodiments, the distal end 408 of the suturing device 400 can be configured to couple with the proximal section 406 of the suturing device 400 after extending around the papillary muscle 400. In some embodiments, the distal end 408 of the suturing device 400 can be configured to couple with the proximal section 406 of the suturing device 400 after extending around the papillary muscle 400 via a magnet. In some embodiments, the coupling of the distal end 408 of the suturing device 400 and the proximal section 406 of the suturing device 400 can facilitate alignment of the suture capture portion 420 and the needle 410.

In some embodiments, a single suturing device 400 can be used to suture the papillary muscle 120 and the papillary muscle 122. In some embodiments, a first suturing device 400 can be used to suture the papillary muscle 120 and a second suturing device 400 can be used to suture the papillary muscle 122.

Figure 6:
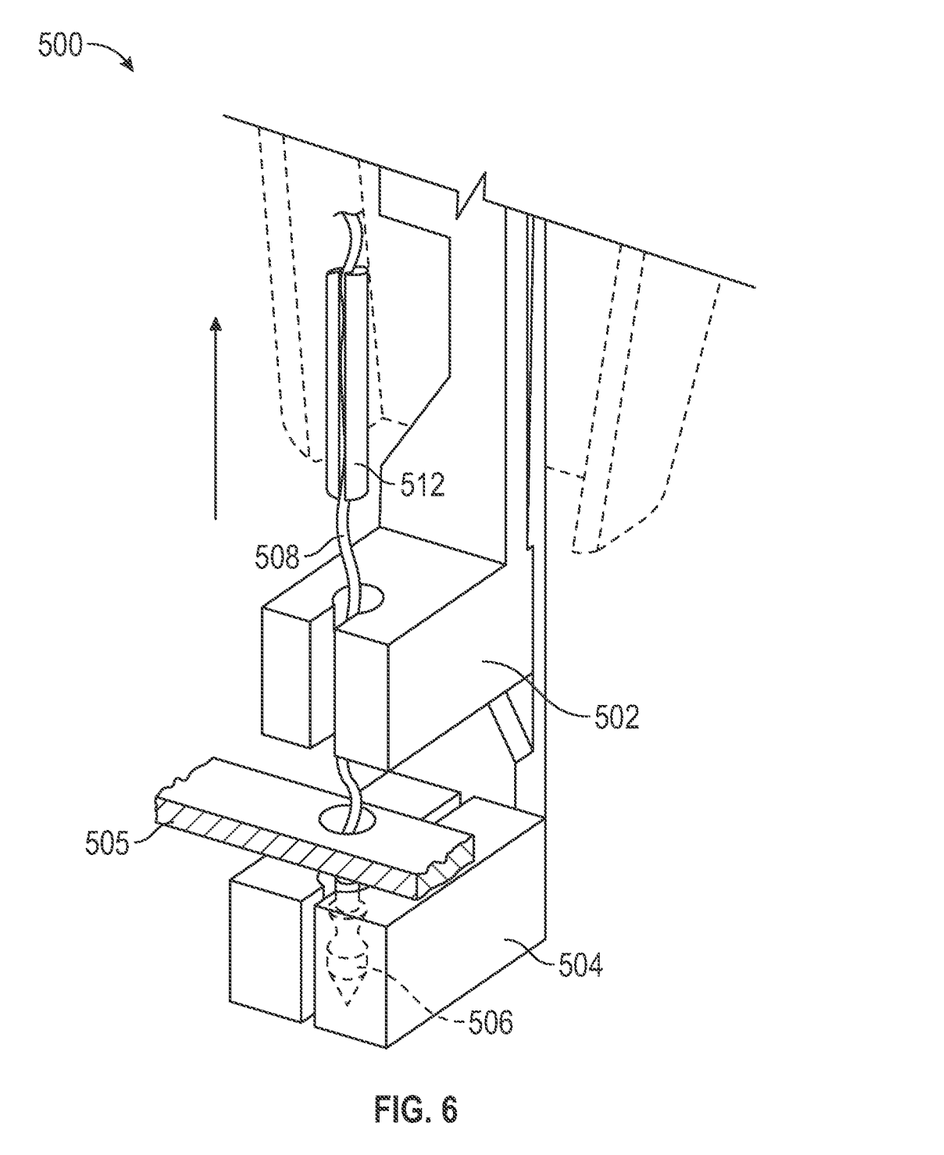
FIG. 6 depicts a schematic representation of a distal portion of a suturing 500 deployed in a tissue 505.

In another embodiment, a papillary suturing device can include a first needle holder configured to receive a needle attached to a suture on a first side of a papillary muscle 120 or 122 and a second needle holder configured to receive the needle attached to the suture on the second side of the papillary muscle 120 or 122. The papillary suturing device can further include a needle driver configured to drive the needle from the first needle holder to the second needle holder and through the papillary muscle so that the suture is drawn through the papillary muscle 120 or 122. In some embodiments after the suture is drawn through the papillary muscle 120 or 122, the first needle holder and second needle holder can be rotated or otherwise moved so that the needle driver can drive the needle from the second needle holder into the first needle holder and through the same papillary muscle or the other papillary muscle. Examples of such suturing devices are described in U.S. Pat. No. 9,398,907, which is hereby incorporated by reference in its entirety.

FIG. 6 shows a portion of a suturing device 500 having a first needle holder 502, a second needle holder 504, and a driver 512. In some embodiments, the driver 512 is configured to drive a needle 506 attached to a suture 508 through a portion of biological tissue 505 and into the second needle holder 504 so that the suture 508 passes through the tissue 505. In some embodiments, the tissue 505 can be one of the papillary muscles 120 and 122. An example of the needle 506 positioned within the second needle holder 504 after passing through the tissue 505 is shown in FIG. 6.

In some embodiments, the first needle holder 502 and second needle holder 504 are rotatable or otherwise movable so that, when the needle 506 is positioned within the second needle holder 504, the driver 512 can drive the needle 506 from the second needle holder 504 into the first needle holder 502. In some embodiments, after the suture 504 is drawn through the papillary muscle 120 or 122 the first needle holder 502 and second needle holder 504 can be rotated or otherwise moved so that the needle drive 512 can drive the needle 506 through the same papillary muscle 120 or 122 or through the other papillary muscle 120 or 122. In some embodiments, a first suturing device 500 can be used to suture the papillary muscle 120 and a second suturing device 500 can be used to suture the papillary muscle 122.

In some embodiments, the suturing device 500 can be advanced into the left ventricle 102 through a transapical approach. In some embodiments, the suturing device 500 can be advanced into the left ventricle 102 through a transseptal approach. In some embodiments, the suturing device 500 can be positioned within the left ventricle 102 so that one of the papillary muscles 120 or 122 is positioned within a gap between the first needle holder 502 and the second needle holder 504 without interfering with the chordae tendineae 128.

After the one or more sutures are drawn through the papillary muscles, for example, using one of the suturing devices 200, 300, 400, and 500 described herein, the one or more sutures can be tightened to draw the papillary muscles 120 and 122 closer to one another. The one or more sutures can then be tied to maintain the position of the papillary muscles 120 and 122.

In some embodiments, more than one of the suturing devices 200, 300, 400, and 500 described herein can be used to suture the papillary muscles 120 and 122. For example, a first suturing device 200, 300, 400, or 500 can be used to suture the papillary muscle 120 and a second suturing device 200, 300, 400, or 500 different than the first suturing device can be used to suture the papillary muscle 122.

In some embodiments, the papillary suturing device can be delivered using a minimally invasive approach (e.g., without open heart surgery). In some embodiments, the suturing device can be delivered into the left ventricle through a transapical approach. In some embodiments, the suturing device can be delivered into the ventricle through a left transseptal approach. In some embodiments, the papillary suturing device can be delivered into the ventricle through the mitral valve.

From the foregoing description, it will be appreciated that inventive suturing devices and methods are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount.

Some embodiments have been described in connection with the accompanying drawings. The figures are not drawn to scale, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims as presented now or in the future.

What is claimed is:

1. A minimally invasive method for suturing papillary muscles, comprising:
   drawing a suture through a first papillary muscle using a needle;
   drawing the suture through a second papillary muscle;
   wrapping a bendable catheter at least partially around the first papillary muscle;
   engaging a distal end of the bendable catheter with a proximal portion of the bendable catheter while the bendable catheter is at least partially wrapped around the first papillary muscle;
   aligning a suture capture portion of the suture with a first side of the first papillary muscle;
   extending the needle through a second side of the first papillary muscle into engagement with the suture capture portion;
   retracting the needle through the first papillary muscle to draw the suture capture portion through the first papillary muscle; and
   tightening the suture to move at least one of the first papillary muscle and the second papillary muscle towards the other of the first papillary muscle and the second papillary muscle,
   wherein aligning the suture capture portion of the suture with the first side of the first papillary muscle comprises aligning a first opening of the bendable catheter with the first side of the first papillary muscle, the first opening of the bendable catheter holding the suture capture portion, and
   wherein extending the needle through a second side of the first papillary muscle into engagement with the suture capture portion comprises advancing the needle from a second opening of the bendable catheter, the second opening being aligned with the second side of the first papillary muscle.

2. The method of claim 1, wherein drawing the suture through the second papillary muscle comprises drawing the suture through the second papillary muscle using the needle.

3. The method of claim 1, wherein the needle is a first needle, wherein drawing the suture through the second papillary muscle comprises drawing the suture through the second papillary muscle using a second needle.

4. The method of claim 1, wherein the method is performed transapically or transseptally.

5. The method of claim 1, further comprising positioning an arm of a suturing device adjacent to the first side of the first papillary muscle, the arm releasably holding the suture capture portion.

6. The method of claim 5, wherein extending the needle through the second side of the first papillary muscle comprises advancing the needle from the suturing device.

7. The method of claim 1, wherein the suture capture portion is a first suture capture portion, the method further comprising:
 aligning a second suture capture portion of the suture with a first side of the second papillary muscle;
 extending the needle through a second side of the second papillary muscle into engagement with the second suture capture portion; and
 retracting the needle through the second papillary muscle to draw the second suture capture portion through the second papillary muscle.

8. The method of claim 1, wherein the suture capture portion is a first suture capture portion, wherein the needle is a first needle, the method further comprising:
 aligning a second suture capture portion of the suture with a first side of the second papillary muscle;
 extending a second needle through a second side of the second papillary muscle into engagement with the second suture capture portion; and
 retracting the second needle through the second papillary muscle to draw the second suture capture portion through the second papillary muscle.

9. The method of claim 1, further comprising:
 driving the needle from a first needle holder positioned on a first side of first papillary muscle to a second needle holder positioned on a second side of the first papillary muscle while the suture is attached to the needle;
 positioning the second needle holder on a first side of the second papillary muscle and the first needle holder on a second side of the second papillary muscle; and
 driving the needle from the second needle holder positioned on the first side of the second papillary muscle to the first needle holder positioned on the second side of the second papillary while the suture is attached to the needle.

* * * * *